(12) United States Patent
Kertser et al.

(10) Patent No.: US 10,925,988 B2
(45) Date of Patent: Feb. 23, 2021

(54) DEVICE, SYSTEM, AND METHOD FOR FILTER RECONSTITUTION

(71) Applicant: ORIDION MEDICAL 1987 LTD., Jerusalem (IL)

(72) Inventors: Michael Kertser, Jerusalem (IL); Konstantin Goulitski, Jerusalem (IL)

(73) Assignee: ORIDION MEDICAL 1987 LTD., Jerusalem (IL)

( * ) Notice: Subject to any disclaimer, the term of this patent is extended or adjusted under 35 U.S.C. 154(b) by 115 days.

(21) Appl. No.: 16/186,865

(22) Filed: Nov. 12, 2018

(65) Prior Publication Data
US 2019/0142984 A1 May 16, 2019

Related U.S. Application Data

(60) Provisional application No. 62/585,284, filed on Nov. 13, 2017.

(51) Int. Cl.
| | |
|---|---|
| *A61L 2/00* | (2006.01) |
| *A61L 9/00* | (2006.01) |
| *A61L 2/20* | (2006.01) |
| *A61L 2/10* | (2006.01) |
| *C01B 13/10* | (2006.01) |
| *B01D 46/00* | (2006.01) |

(52) U.S. Cl.
CPC ............... *A61L 2/202* (2013.01); *A61L 2/10* (2013.01); *C01B 13/10* (2013.01); *A61L 2202/11* (2013.01); *A61L 2202/24* (2013.01); *B01D 46/006* (2013.01)

(58) Field of Classification Search
CPC ... A61L 9/20; A61L 2/20; A61L 2/202; A61L 2/02; A61L 2/022; A61L 2/10
USPC .......................................................... 422/24
See application file for complete search history.

(56) References Cited

U.S. PATENT DOCUMENTS

| | | | |
|---|---|---|---|
| 9,358,316 B2 * | 6/2016 | Leyva | ................... A61M 16/16 |
| 2006/0145871 A1 | 7/2006 | Donati et al. | |

FOREIGN PATENT DOCUMENTS

| | | |
|---|---|---|
| WO | 2012161981 A1 | 11/2012 |
| WO | 2014060051 A1 | 4/2014 |

OTHER PUBLICATIONS

International Application No. PCT/IL2018/051217 International Search Report and Written Opinion dated Feb. 27, 2019, 10 pages (MD40052PCT).

* cited by examiner

*Primary Examiner* — Monzer R Chorbaji
(74) *Attorney, Agent, or Firm* — Cantor Colburn LLP

(57) ABSTRACT

A device for reconstituting a filter and/or a filter-containing consumable for use in breath monitoring, the device including a connector socket that may receive and/or mate with the filter or filter-containing consumable, a pump that may pump ambient air into a chamber of the device, an inlet that may allow flow of oxygen into the chamber, a UV source that may catalyze the formation of ozone from the oxygen, thereby obtaining ozone enriching air in the chamber, and an outlet that may eject the ozone enriched air, from the chamber, into the filter, thereby reconstituting the filter and/or the filter-containing consumable.

20 Claims, 3 Drawing Sheets

DEVICE, SYSTEM, AND METHOD FOR FILTER RECONSTITUTION

CROSS-REFERENCE TO RELATED APPLICATION

This application claims priority to and the benefit of U.S. Provisional Application No. 62/585,284, entitled "DEVICE, SYSTEM AND METHOD FOR FILTER RECONSTITUTION," filed Nov. 13, 2017, the content of which is incorporated herein by reference in its entirety for all purposes.

TECHNICAL FIELD

The present disclosure generally relates to a fluid filtering device that includes a mechanism configured to block reuse thereof.

BACKGROUND

This section is intended to introduce the reader to various aspects of art that may be related to various aspects of the present techniques, which are described and/or claimed below. This discussion is believed to be helpful in providing the reader with background information to facilitate a better understanding of the various aspects of the present disclosure. Accordingly, it should be understood that these statements are to be read in this light, and not as admissions of prior art.

Some breath sampling tubes with inline filters are capable of containing a maximum amount of liquids (e.g., approximately 135 microliters [($\mu$L)]). Once a maximum absorption and/or accumulation limit has been reached, a $CO_2$ monitor (e.g., capnograph) will detect a pressure drop. As a result, medical staff may receive an alert to change consumables (e.g., breath sampling tubes and inline filters), and the $CO_2$ monitor may cease working in order to protect it from being damaged by entrance of liquids. However, unauthorized reuse of the sampling line and inline filter has been observed. There is thus a need for a device and method for reconstituting filters, while ensuring patient safety.

SUMMARY

A summary of certain embodiments disclosed herein is set forth below. It should be understood that these aspects are presented merely to provide the reader with a brief summary of these certain embodiments and that these aspects are not intended to limit the scope of this disclosure. Indeed, this disclosure may encompass a variety of aspects that may not be set forth below.

The present disclosure relates to devices, systems, and methods for reconstituting filters. More particularly, the present disclosure relates to reconstituting filters incorporated into breath monitoring consumables (e.g., breath sampling tubes).

According to some embodiments, the devices may include a chamber that may receive ambient air and oxygen and eject oxygen enriched air and/or ozone into a used filter, such that the ejected ozone dries and/or disinfects the filter. This may advantageously cause the filter and/or the filter containing breath sampling tube to be properly reconstituted prior to being reused.

According to some embodiments, the device may mark the consumable, once properly reconstituted thereby. According to some embodiments, the marking (e.g., tagging or labeling) of the consumable may be visible to medical staff, the patient, and/or the patient's surroundings, such that users in the vicinity of the consumable may be informed that the filter has been reconstituted in the manner disclosed herein. As used herein, the term "consumable" is intended to denote a filter, a breath sampling tube, or both, that is replaced after a predetermine amount of time and/or reaching a predetermined threshold (e.g., a maximum amount of absorbed fluid).

According to some embodiments, the device may be configured to adjust the flow of oxygen into the chamber, the volume of oxygen enriched air ejected through the outlet, and/or the flow pressure of the oxygen enriched air into the filter/filter-containing consumable, depending on the type of filter and/or type of filter-containing consumable connected to the at least one connector socket and/or depending on the number of filters and/or filter-containing consumables connected to the device. This may advantageously ensure versatile use of the device for filters and/or filter-containing consumables of different characteristics (e.g., length, diameter).

According to some embodiments, there is provided a device for reconstituting a filter and/or a filter-containing consumable for use in breath monitoring, the device including at least one connector socket that may receive and/or mate with the filter or filter-containing consumable, a pump that may pump ambient air into a chamber of the device, an inlet that may enable flow of oxygen into the chamber, a UV source that may catalyze the formation of ozone, thereby obtaining ozone-enriched air, and an outlet that may eject the ozone-enriched air from the chamber into a used filter, thereby reconstituting the used filter and/or the used filter-containing consumable to generate a reusable filter and/or filter-containing consumable.

According to some embodiments, the UV source may be or include a low-pressure UV lamp.

According to some embodiments, the UV source may decompose organic compounds present in the chamber and/or the ambient air.

According to some embodiments, the device may include a mechanism that may mark the used filter and/or the filter-containing consumable when the used filter and/or the filter containing consumable has been reconstituted.

According to some embodiments, the ozone-enriched air may be ejected at high pressure.

According to some embodiments, the device may include at least two connectors, each connector may receive a consumable of different length.

According to some embodiments, the device may further include a controller (e.g., electronic controller) that may control the flow of oxygen into the chamber, the volume of ozone-enriched air ejected through the outlet, and/or the flow pressure of the ozone-enriched air, depending on the type of filter and/or type of filter-containing consumable connected to the at least one connector socket and/or depending on the number of filters and/or filter-containing consumables connected to the device.

According to some embodiments, there is provided a system for reconstituting a filter for use in breath monitoring and/or a consumable including same that has been previously used, the system including a filter and/or filter-containing consumable having a connector and a device for reconstituting the previously used filter and/or filter-containing consumable. The device includes at least one connector socket that may receive and/or mate with the connector, a pump that may pump ambient air into a chamber of the device, an inlet that may allow flow of oxygen into the chamber, a UV source that may catalyze the formation of ozone, thereby obtaining ozone-enriched air, and an outlet that may eject the ozone-enriched air from the chamber into the filter, thereby reconstituting the previously used filter and/or the filter-containing consumable to generate a reusable filter and/or filter-containing consumable.

According to some embodiments, the system may include an ozone filter that may block ozone from being released into the surroundings.

According to some embodiments, there is provided a method for reconstituting a previously used filter for use in breath monitoring and/or a previously used filter-containing consumable, the method including connecting a previously used filter and/or filter-containing consumable to a connector socket of a filter reconstituting device, injecting ambient air into a chamber of the device using a pump, generating a flow of oxygen into the chamber of the device, catalyzing formation of ozone using a UV lamp, such that the ambient air be enriched with ozone, and ejecting the ozone-enriched air into the filter and/or filter-containing consumable, thereby at least partially reconstituting the filter.

According to some embodiments, the method may include marking (e.g., tagging or labeling) the filter and/or the filter-containing consumable, when the filter and/or the filter-containing consumable has been reconstituted (e.g., in response to the filter and/or the filter-containing consumable being reconstituted).

According to some embodiments, the method may include blocking oxygen-enriched air from being released into the surroundings via a dedicated filter.

According to some embodiments, the UV source may be or include a low-pressure UV lamp. According to some embodiments, the UV lamp may decompose organic compounds present in the chamber and/or the ambient air.

According to some embodiments, the oxygen-enriched air may be ejected at high pressure.

According to some embodiments, the method may include controlling (e.g., via an electronic controller) the flow of oxygen into the chamber, the volume of oxygen enriched air ejected through the outlet and/or the flow pressure of the oxygen-enriched air ejected, depending on the type of filter and/or type of filter-containing consumable connected to the at least one connector socket and/or depending on the number of filters and/or filter-containing consumables connected to the device.

Certain embodiments of the present disclosure may include some, all, or none of the above advantages. One or more technical advantages may be readily apparent to those skilled in the art from the figures, descriptions and claims included herein. Moreover, while specific advantages have been enumerated above, various embodiments may include all, some or none of the enumerated advantages.

In addition to the exemplary aspects and embodiments described above, further aspects and embodiments will become apparent by reference to the figures and by study of the following detailed descriptions.

BRIEF DESCRIPTION OF THE FIGURES

Various exemplary embodiments are illustrated in the accompanying figures with the intent that these examples not be restrictive. It will be appreciated that for simplicity and clarity of the illustration, elements shown in the figures referenced below are not necessarily drawn to scale. Also, where considered appropriate, reference numerals may be repeated among the figures to indicate like, corresponding, or analogous elements. Of the accompanying figures.

DETAILED DESCRIPTION

Figure 1:
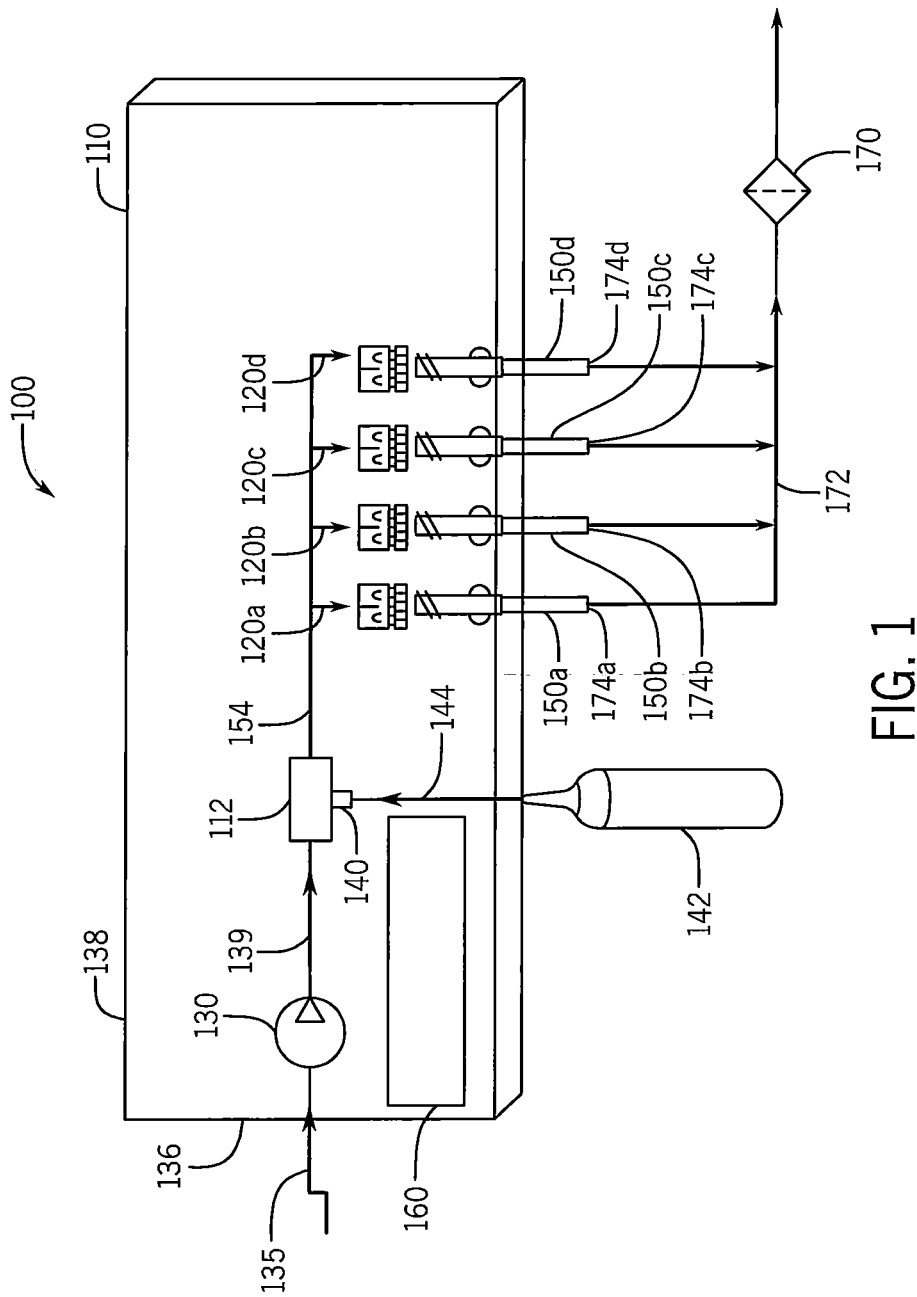
FIG. 1 schematically illustrates a system for reconstituting filters and/or filter-containing consumables, according to some embodiments of the present disclosure.

One or more specific embodiments of the present disclosure will be described below. These described embodiments are only examples of the presently disclosed techniques. Additionally, in an effort to provide a concise description of these embodiments, all features of an actual implementation may not be described in the specification. It should be appreciated that in the development of any such actual implementation, as in any engineering or design project, numerous implementation-specific decisions must be made to achieve the developers' specific goals, such as compliance with system-related and business-related constraints, which may vary from one implementation to another. Moreover, it should be appreciated that such a development effort might be complex and time consuming, but may nevertheless be a routine undertaking of design, fabrication, and manufacture for those of ordinary skill having the benefit of this disclosure.

According to some embodiments, there is provided a device for reconstituting a filter that has previously been used and/or a filter-containing consumable for reuse in medical devices, such as breath monitors (e.g. $CO_2$ monitors or capnographs), medical ventilators, or the like.

As used herein, the term "filter" may refer to any type of filter that may absorb, pass, evaporate, or otherwise dehumidify liquids from gasses flowing therethrough. According to some embodiments, the filter may be any type of filter utilized in breath monitoring tubes, oxygen supply tubes, or the like. According to some embodiments, the filter may be a Nafion® filter, a hydrophobic filter, a hydrophilic filter, a heat and moisture exchanger (HME), a heat and moisture exchanger filter (HMEF), or any combination thereof. As used herein, the term "filter-containing consumable" may refer to any consumable having a filter (e.g., any of the above-mentioned filters) incorporated therein or configured to be used in conjunction with a filter. Non-limiting examples of filter-containing consumables include a breath sampling tube, a nasal/oral cannula, a bite-block adapter consumable, or the like. Each possibility is a separate embodiment.

As used herein, the term "reconstituting" may refer to making a previously used filter and/or filter-containing consumable fit for reuse. According to some embodiments, reconstituting a filter and/or a filter-containing consumable may include drying, cleaning, disinfecting, decomposing, and/or any other suitable measure that may make the filter and/or a filter-containing consumable fit for reuse. According to some embodiments, the reconstituted filter and/or the filter-containing consumable may be suitable for reuse with the same and/or different patients.

According to some embodiments, the device may include at least one connector socket that may receive the filter or the filter-containing consumable. As used herein, the term "connector socket" may refer to a socket that may specifically (e.g., via connector mating) receive a connector of the filter and/or the filter-containing consumable, such as, but not limited to, a breath sampling tube connector. Additionally or alternatively, the connector may be a universal connector configured to hold, clamp, or otherwise stabilize the filter and/or the filter-containing consumable in a manner enabling its reconstitution (e.g., allowing air to be injected into the filter and/or the filter-containing consumable, at high pressure). For example, the air may be injected into the filter and/or filter-containing consumable at a pressure suitable to support and maintain positive air flow over the flow restriction that may be cause by the connected filter and/or filter-containing consumable. By way of non-limiting example, the pressure may be at or above 15 pounds per square inch (psi) (1 atmosphere (atm)). However, any other suitable pressure may be used.

In certain embodiments, the connector socket has a feature that is configured to couple to a complementary feature on the filter or the filter-containing consumable (e.g., male to female coupling or vice versa). In certain embodiments, the connector socket may be a female connector that mates with a male connector on the filter or filter containing consumable. The mating between the connector socket and the connector on the filter may be a snap fit connection or an interference fit connection. In other embodiments, a clamp may be used to secure the connector socket to the connector of the filter or the filter containing consumable. In one embodiment, the connector socket and the connector of the filter may have a threaded connection. For example, the connector socket may include a threaded ring that, when rotates, is secured to a threaded portion on the connector of the filter or the filter-containing consumable. In other embodiments, a socket of the connector socket is threaded such that, when an end of the connector of the filter or the filter-containing consumable is rotates, threads on the end of the connector engage with the threads in the socket of the connector socket to secure the filter or the filter-containing consumable to the connector socket.

According to some embodiments, the device may include at least 2, at least 4, at least 10, at least 20, at least 50, or at least 100 connector sockets, each connector socket receives a respective filter or filter-containing consumable. Each implementation may be a separate embodiment. According to some embodiments, each connector socket may include a valve that may block outflow of ozonized air (e.g., ozone-enriched air) when no filter and/or filter-containing consumable is connected thereto. According to some embodiments, each connector socket may include an ozone filter that may block ozone from being ejected into the surroundings when no filter and/or filter-containing consumable is connected thereto. According to some embodiments, the ozone filter may be removed when the filter and/or the filter-containing consumable is connected thereto.

According to some embodiments, the device may further include a pump that may pump ambient air into a chamber of the device. According to some embodiments, the pump may pump the ozonized air through the at least one connector socket to which the filter or the filter-containing consumable is connected. Alternatively, the device may include an additional pump that may pump the ozonized air through the at least one connector socket to which the filter or the filter-containing consumable is connected. According to some embodiments, the pump and/or the additional pump may enable and/or cause the ozonized air to flow through the filter and/or the filter-containing consumable at a determined flow rate regardless of the number of filters and/or filter-containing consumables connected to the device.

According to some embodiments, the device may itself be the chamber. Alternatively, the chamber may be a dedicated compartment within the device. According to some embodiments, the device and/or the chamber may be a pneumatic system.

According to some embodiments, the device may further include an inlet that may allow flow of oxygen into the chamber. According to some embodiments, the flow of oxygen into the chamber may be controllable, for example by a controller (e.g., electronic controller).

According to some embodiments, the device may include a UV source that may catalyze the formation of ozone, thereby enriching the air in the chamber with ozone. According to some embodiments, the ozonized air may include sufficient ozone to ensure proper sterilization of the filter. According to some embodiments, the ozonized air may include 0.01 to 0.20 volume/volume percent (v/v percent) ozone ($O_3$). According to some embodiments, the UV source may be a low-pressure or medium-pressure mercury (Hg) UV lamp. According to some embodiments, the UV source may be ozone-generating and/or disinfecting. According to some embodiments, a UV low/medium pressure lamp may be made of quartz glass or synthetic quartz glass. According to some embodiments, 40 percent of the electrical power of the UV lamp may be used as 254 nanometers (nm) UVC radiation to disinfect water and air. If synthetic quartz glass is used as the lamp material, 185 nm UV radiation (vacuum UV) may be emitted in addition for oxidation processes, such as the decomposition of pollutants, odors, and/or greases.

According to some embodiments, the device may include an outlet that may eject the ozone-enriched air, from the chamber into and/or through the filter, thereby reconstituting the filter and/or the filter-containing consumable. According to some embodiments, the oxygen-enriched air may be ejected and/or passed through the filter and/or the filter-containing consumable at a pressure suitable to overcome air flow resistance that may be caused by the connected filter and/or filter-containing consumable.

According to some embodiments, the device may include a mechanism that may mark the filter and/or the filter containing consumable when the filter and/or the filter containing consumable has been reconstituted. It is understood that the marking may be any marking which may serve as an indicator of proper filter reconstitution. As a non-limiting example, the marking may include adding a label, optionally including a text such as "reconstituted," "approved for use," or the like. As another non-limiting example, the marking may include adding a radio-frequency identification (RFID) tag indicative of proper reconstitution. As another non-limiting example, the marking may include printing, engraving, carving, coloring, or otherwise adding a marker on the filter and/or the filter-containing consumable indicative of it being reconstituted according to the techniques disclosed herein. Each possibility is a separate embodiment. According to some embodiments, a micro-chip encoder, molded into or onto the consumable PVC connector, may serve as a marker.

In certain embodiments, the filter may include a color indicator to alert a caregiver that the filter is saturated with absorbed fluids. During reconstitution of the filter according to the present disclosure, the color indicator may change color to indicate that the filter has been reconstituted and is ready for reuse. For example, the ozone supplied to the filter may cause the color indicator to change from a color associated with a used state to a color associated with an unused or reconstituted state. In certain embodiments, the used state may be associated with a lack of color or a lack of visible color indicator. In this way, the visible color change or the presence of a visible color indicator may be used as a marker indicative of the reusable nature of the filter or the filter-containing consumable.

According to some embodiments, the device may further include a controller that may control the flow of oxygen into the chamber, control the volume of oxygen-enriched air ejected through the outlet and/or the duration of the ozone treatment. According to some embodiments, the controller may define the flow rate and/or volume of the oxygen-enriched air ejected through the outlet based on the number of filters and/or the filter-containing consumables connected to the device. According to some embodiments, the controller may define the flow rate and/or volume of the oxygen-enriched air ejected through the outlet based on the type of filter and/or filter-containing consumable connected to the device (e.g., the length of the filter and/or of the filter-containing consumable, the diameter of the filter and/or of the filter-containing consumable, or any other parameter).

According to some embodiments, there is provided a system for reconstituting a filter and/or a filter-containing consumable for use in medical devices, such as breath monitors (e.g. $CO_2$ monitors or capnographs), medical ventilators, and the like. The system includes the filter and/or the filter containing consumable with a connector, and the system also includes a device for reconstituting the filter and/or the filter-containing consumable, as essentially described herein.

According to some embodiments, the system may further include an ozone filter that may prevent ozonized air from exiting the filter and/or the filter-containing consumable at the other end thereof. According to some embodiments, the entire filter and/or the filter-containing consumable may be held within the device. Alternatively, the filter and/or the filter-containing consumable or the end thereof opposite the connector may be held within a container that may block ozonized air from being released into the surroundings.

According to some embodiments, there is provided a method for reconstituting a filter and/or a filter-containing consumable for medical use. The method includes connecting the filter and/or the filter-containing consumable to a connector socket of a device for reconstituting filters and/or filter-containing consumables. The method also includes injecting ambient air into a chamber of the device using a pump, flowing oxygen into the chamber of the device, catalyzing the formation of ozone using a UV lamp, such that the ambient air is enriched with ozone. The method also includes ejecting the oxygen-enriched air into the filter and/or the filter-containing consumable, thereby at least partially reconstituting the filter.

According to some embodiments, the method may be performed using the herein disclosed device for reconstituting a filter and/or a filter-containing consumable.

According to some embodiments, the method may further include marking the filter and/or the filter-containing consumable when the filter and/or the filter containing consumable has been reconstituted. The marking may include carving, printing, coloring, tagging, labelling, or otherwise adding a visible note indicating that a complete reconstitution of the filter according the techniques disclosed herein has taken place.

According to some embodiments, the method may further include blocking oxygen-enriched air from being released into the surroundings by utilizing a dedicated filter. According to some embodiments, an ozone filter may removably be placed at the outlet of each connector, such that when no connector is connected to the connector socket, ozonized air is blocked from being released into the surroundings.

According to some embodiments, the oxygen-enriched air may be ejected and/or sent through the filter and/or the filter containing consumable at high pressure.

According to some embodiments, the method may include controlling the flow of oxygen into the chamber, the volume of oxygen enriched air ejected through the outlet, and/or the flow pressure thereof. According to some embodiments, controlling the flow of oxygen may include defining the flow rate and/or volume of the oxygen enriched air ejected into and/or through the filter and/or the filter-containing consumable, based on the type of filter and/or filter-containing consumable connected to the device (e.g. the length of the filter and/or of the filter-containing consumable, the diameter of the filter and/or of the filter-containing consumable, or any other parameter). According to some embodiments, controlling the flow of oxygen may include defining the flow rate and/or volume of the oxygen-enriched air ejected into and/or through the filter and/or the filter-containing consumable based on the number of filters and/or the filter-containing consumables connected to the device.

Reference is now made to FIG. 1, which schematically illustrates a system 100 for reconstituting a filter and/or a filter-containing consumable of medical devices, according to some embodiments. A system 100 includes a device 110, which may be used to carry out the drying-out, cleaning, and/or disinfecting for reconstituting the filter and/or the filter-containing consumable in a manner that renders the filter and/or filter-containing consumable suitable for medical reuse. The device 110 includes a plurality of connector sockets, here illustrated as connector sockets 120a-120d, each connector socket 120 allows connection of a filter and/or a filter-containing consumable 150a-150d thereto, at the same or different times. In certain embodiments, each connector socket 120 is connected to a respective filter and/or filter-containing consumable 150. In other embodiments, only a portion of the connector sockets 120 are connected to a respective filter and/or filter-containing consumable 150.

As discussed above, the connector socket may include certain features to facilitate connection of the filter and/or filter-containing consumable. The connection between the connector socket 120 and the filter and/or filter-containing consumable 150 may be a luer connection. For example, the connector socket 120 may include a female connector that engages with a male connector of the filter and/or the filter-containing consumable 150 to secure the filter and/or the filter-containing consumable 150 to the system 100 via a snap fit or interference fit connection. In certain embodiments, a clamp may be used to couple and secure the filter and/or the filter-containing consumable 150 to the connector socket 120. In other embodiments, the connector socket 120 may include a threaded portion that engages with a complementary threaded portion on the filter and/or the filter-containing consumable 150 to secure the filter and/or filter-containing consumable 150 to the connector socket 120. As should be noted any other connector socket configuration that is compatible with a connector of the filter and/or the filter-containing consumable 150 may be used to secure the filter and/or the filter-containing consumable 150 to the system 100.

The device 110 may be a pneumatic system connected to a pump 130 that may inject ambient air 135 into a chamber 112 of the device 110. For example, the device 110 may include an air inlet 136 that facilitates a flow of the ambient air 135 into a housing 138 of the device 110. The chamber 112, the pump 130, and the connector sockets 120 are housed within the housing 138 of the device 110. The pump 130 directs the ambient air 132 to the chamber 112 via an ambient air flow line 139 fluidly coupling the chamber 112 to the pump 130. While in the chamber 112, the ambient air 135 is enriched with ozone.

For example, the chamber 112 includes an inlet 140 that may receive oxygen from an oxygen source 142. The oxygen source 142 may include a portable oxygen tank or may be from a central oxygen source. The inlet 140 and/or an inlet tubing 144 may deliver the oxygen from the oxygen source 142 to the chamber 112. For example, the inlet tubing 144 fluidly couples the inlet 140 of the chamber 112 to the oxygen source 142. Oxygen from the oxygen source 142 is converted into ozone via a light catalyzed radical reaction. For example, the device 110 may include an ultraviolet (UV) source 160 (e.g., a low-pressure UV lamp) that may emit UV light at a wavelength and power capable of catalyzing a radical reaction of the oxygen to generate ozone, such that the ambient air 135 pumped into the chamber 112 will be enriched with ozone (e.g. 0.01 to 0.20 v/v percent ozone). In certain embodiments, the UV source 160 may decompose organic material present in the chamber 112, the inlet 140, and/or the inlet tubing 144, thereby disinfecting the chamber 112, the inlet 140, and/or the inlet tubing 144 prior to and/or during the reconstitution process.

The ozone-enriched air in the chamber 112 may be pressurized so as to create a necessary flow of the ozone-enriched air into the filter and/or the filter-containing consumable 150a-150d, thereby drying and disinfecting the line and making them suitable for reuse. The filter and/or filter containing consumable 150 may be flushed with ozone-enriched air for approximately 30 minutes to 2 hours to ensure sterilization and reconstitution. However, the filter and/or filter-containing consumable 150 may be flushed with the ozone-enriched air for any other suitable amount of time. For example, the connector sockets 120 are positioned with a housing 138 of the device 110 and fluidly coupled to an ozone flowline 154. The ozone flowline 154 directs the ozone-enriched air into the filter and/or filter-containing consumable 150 coupled to the respective connector socket 120. The housing 138 may include openings along an exterior that are aligned with the connector sockets 120 such that the connector of the filter and/or filter-containing consumable 150 may be inserted into the opening and coupled to the respective connector socket 120. In certain embodiments, and adapter may be used to couple the connector socket 120 with the connector of the filter and/or the filter-containing consumable 150 (e.g., if the connector socket 120 is not compatible with the connector of the filter and/or the filter-containing consumable 150).

According to some embodiments, the system 100 may further include one or more ozone filters 170 positioned downstream of the chamber 112 that may block ozonized air from being released into the surroundings after use. For example, in the illustrated embodiment, the ozone filter 170 is positioned along a discharge flowline 172 fluidly coupled to an outlet 174 or each respective filter and/or filter-containing consumable 150. The discharge flowline 172 receives the fluid exiting the filter and/or the filter-containing consumable 150 after use and captures, via the ozone filter 170, any remaining ozone in the fluid before the fluid is released from the device 110. In certain embodiments, an additional ozone filter 170 may be positioned adjacent to one or more connector sockets 120 when not in use. For example, an adapter having the ozone filter 170 may be connected to the connector socket 120 when not in used to capture ozone that may leak out through the unused connector sockets 120 during use of the device 110.

Figure 2A:
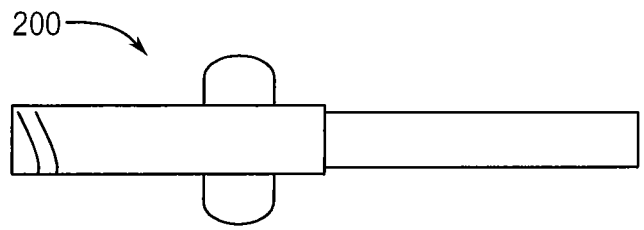
FIG. 2A schematically illustrates part of a filter-containing consumable prior to being reconstituted, according to some embodiments of the present disclosure.
Figure 2B:
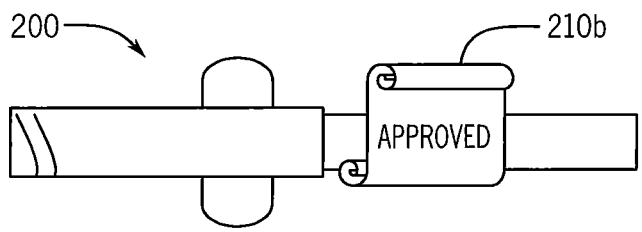
FIG. 2B schematically illustrates the part of the filter-containing consumable of FIG. 2A after having been reconstituted, including a label indicative thereof, according to some embodiments of the present disclosure.
Figure 2C:
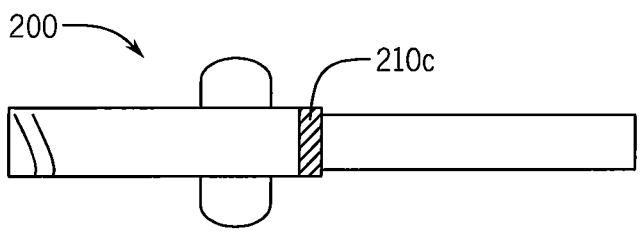
FIG. 2C schematically illustrates the part of the filter-containing consumable of FIG. 2A after having been reconstituted, including a tag indicative thereof, according to some embodiments of the present disclosure.
Figure 2D:
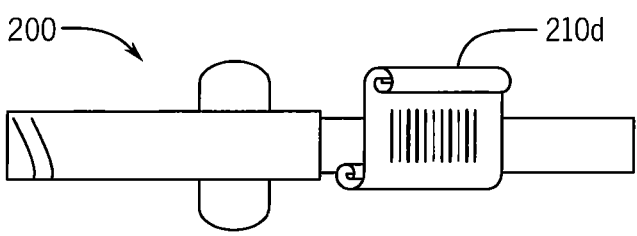
FIG. 2D schematically illustrates the part of the filter-containing consumable of FIG. 2A after having been reconstituted, including a radio-frequency identification (RFID) tag indicative thereof, according to some embodiments of the present disclosure.

Reference is now made to FIGS. 2A, 2B, 2C, and 2D which schematically illustrate a part of a filter-containing consumable 200 before (FIG. 2A) and after (FIG. 2B-D) having been reconstituted, according to some embodiments. Once reconstituted, the filter-containing consumable 200 may be labeled or marked in any of multiple ways. Non-limiting examples of suitable ways of marking the filter-containing consumable 200 are illustrated in FIGS. 2B-D. For example, in one embodiment, a label 210b indicative of ozone treatment or reconstitution may be attached to the filter-containing consumable 200, as shown in FIG. 2B. The label 210b may have a color tag (e.g., red, green blue, yellow, orange, or any other suitable color) or other marking that is indicative of the filter-containing consumable 200 being reconstituted and reusable. In certain embodiments, the label 210b may include text, such as "approved," indicating that the filter-containing consumable 200 has been reconstituted in a manner approved for medical use. As another example, a tag, such as a printed pattern 210c as shown in FIG. 2C, indicating that the filter-containing consumable 200 has been reconstituted in a manner approved for medical use may be attached to the filter-containing consumable 200. The printed pattern 210c may include any desired shape and/or pattern including, but not limited to, hash marks, circles, diamonds, squares, lines, etc. As another example, a radio-frequency identification (RFID) tag 210d may be attached to the filter-containing consumable 200, as shown in FIG. 2D. The RFID tag 210d may encode a unique identification number that is readable by an RFID reader and that indicates that the filter-containing consumable 200 has been reconstituted in a manner approved for medical use. In another embodiment, the RFID tag is a read/write tag that is configured to permit writing of an indication of reconstitution.

As discussed above, the filter in the filter-containing consumable may include a color indicator. Accordingly, during reconstitution of the filer-containing consumable 200, the filter may change colors when the filter has been reconstituted and is ready for reuse. The filter may contain a substance that reacts with the ozone during reconstitution and sterilization. The reaction between the substance and the ozone may cause a color change, thereby indicating that the filter-containing consumable 200 is ready for reuse.

Figure 3:
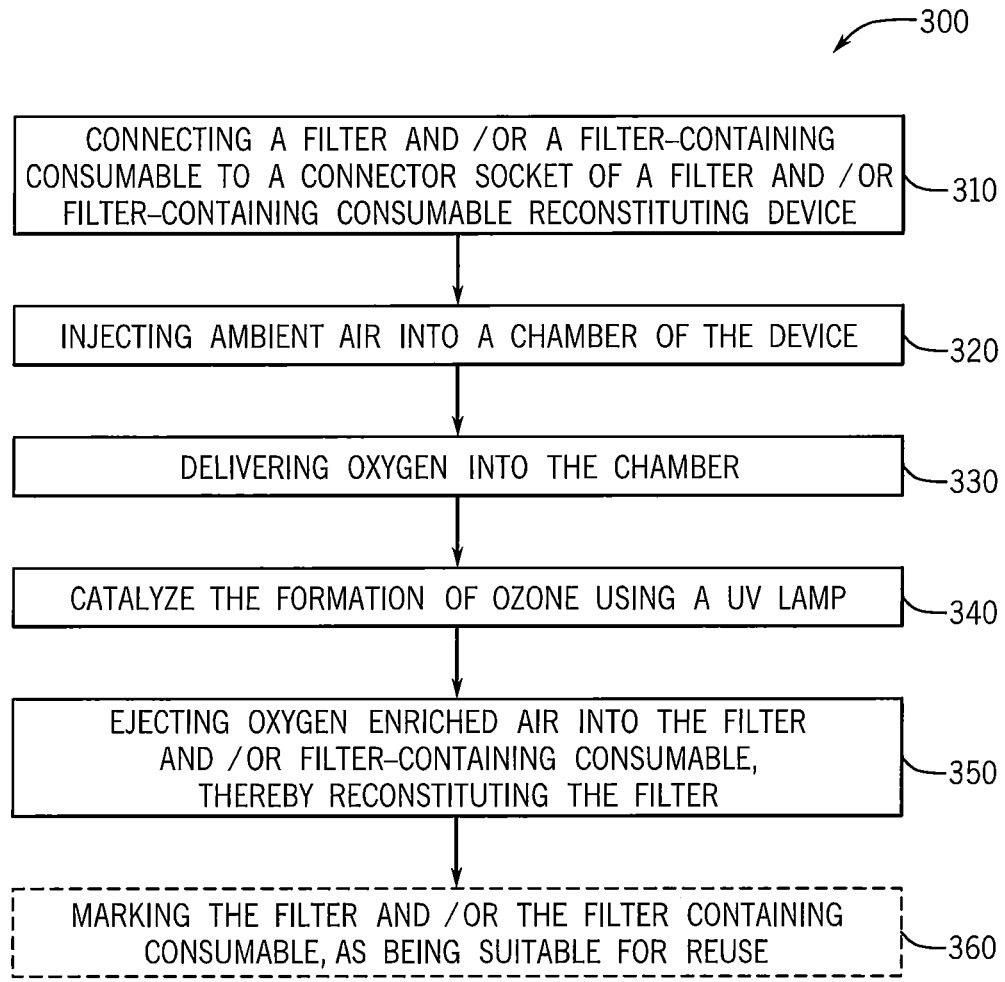
FIG. 3 is an illustrative flow chart of a method for reconstituting a filter and/or a filter-containing consumable for medical reuse, according to some embodiments of the present disclosure.

Reference is now made to FIG. 3, which is an illustrative flow chart of a method 300 for reconstituting a filter and/or a filter-containing consumable for medical use, according to some embodiments. Step 310 of the method includes connecting a filter and/or a filter-containing consumable to a connector socket of a device for reconstituting filters and/or filter-containing consumables. For example, the filter and/or filter-containing consumable may be connected to the connector socket via a luer connection, snap fit, interference fit, threaded connection, clamping, or any other suitable reversible connection. In step 320, ambient air is injected into a chamber of the device, for example by utilizing a pump. In step 330 oxygen is allowed entrance and/or injected into the chamber of the device. In step 340, ozone is generated using UV radiation (e.g., via a low-pressure UV lamp). For example, the low-pressure UV lamp may irradiate a stream of oxygen flowing from an oxygen source into the chamber of the device. The UV light emitted from the low-pressure UV lamp may catalyze a radical reaction to convert at least a portion of the oxygen into ozone. As a result, the ambient air within the chamber is ozonized and/or ozone-enriched. In step 350, the ozone-enriched air is injected, for example, at a pressure that is sufficient to provide a suitable flow of the ozone-enriched air through the filter and/or filter-containing consumable, thereby drying-out, cleaning, and/or disinfecting the filter and/or filter-containing consumable and making it suitable for medical reuse (e.g., for use with the same or a different patient). The pressure may vary depending on the number of filter and/or filter-containing consumables connected to the device for reconstituting filters and/or filter-containing consumables. The filter and/or the filter-containing consumable may be exposed to the ozone-enriched air for between approximately 30 to 120 minutes or more, after which the filter and/or filter-containing consumable is considered reconstituted and reusable.

According to some embodiments, the method may further include an additional step 360 marking the filter and/or the filter containing consumable, as being fully reconstituted and suitable for medical reuse. The marking may include carving, printing, coloring, tagging, labelling, or otherwise adding a visible note indicating that a complete reconstitution of the filter has taken place (e.g., the reconstitution as essentially described herein). For example, the device for reconstituting filters may include a tagging feature (e.g., a label maker, a stylus) that automatically tags and/or marks the filter and/or filter-containing consumable after reconstituting. In other embodiments, a user of the device may manually tag the filter and/or the filter-containing consumable after being reconstituted.

It should be appreciated that, according to some embodiments, the method may include an additional step of blocking oxygen-enriched air from being released into the surroundings by utilizing a dedicated filter. According to some embodiments, the method may also include a step of controlling the flow of oxygen into the chamber, the volume of oxygen-enriched air ejected through the outlet, and/or the flow pressure thereof. According to some embodiments, controlling the flow of oxygen may include defining the flow rate and/or volume of the oxygen enriched air ejected into and/or through the filter and/or the filter containing consumable based on the type of filter and/or filter-containing consumable connected to the device (e.g., the length of the filter and/or of the consumable, the diameter of the filter and/or of the consumable, or any other parameter). According to some embodiments, controlling the flow of oxygen may include defining the flow rate and/or volume of the oxygen-enriched air ejected into and/or through the filter and/or the filter containing consumable based on the number of filters and/or the filter-containing consumables connected to the device.

The terminology used herein is for the purpose of describing particular embodiments only and is not intended to be limiting. As used herein, the singular forms "a," "an," and "the" are intended to include the plural forms as well, unless the context clearly indicates otherwise. It will be further understood that the terms "comprises" or "comprising," when used in this specification, specify the presence of stated features, integers, steps, operations, elements, or components, but do not preclude or rule out the presence or addition of one or more other features, integers, steps, operations, elements, components, or groups thereof. According to some embodiments, the term "comprising" may be replaced by the term "consisting essentially of" or "consisting of."

While a number of exemplary aspects and embodiments have been discussed above, those of skill in the art will recognize certain modifications, additions and sub-combinations thereof. It is therefore intended that the following appended claims and claims hereafter introduced be interpreted to include all such modifications, additions, and sub-combinations as are within their true spirit and scope.

The invention claimed is:

1. A device for reconstituting a filter and/or a filter-containing consumable for use in breath monitoring, the device comprising:
   at least one connector socket configured to receive and/or mate with the filter or the filter-containing consumable;
   a pump configured to pump ambient air into a chamber of the device;
   an inlet configured to allow a flow of oxygen into the chamber,
   an ultraviolet (UV) source configured to catalyze formation of ozone from the oxygen, thereby generating ozone-enriched air in the chamber; and
   an outlet configured to eject the ozone-enriched air from the chamber and into the filter and/or the filter-containing consumable, thereby reconstituting the filter and/or the filter-containing consumable.

2. The device of claim 1, wherein the UV source comprises a low-pressure UV lamp.

3. The device of claim 1, wherein the UV source is configured to decompose organic compounds present in the chamber, in the ambient air, or both.

4. The device of claim 1, comprising a mechanism configured to mark the filter and/or the filter-containing consumable after the filter and/or the filter-containing consumable has been reconstituted.

5. The device of claim 1, wherein the ozone-enriched air is ejected at high pressure.

6. The device of claim 1, wherein the at least one connector socket comprises a first connector socket and a second connector socket, the first connector socket is configured to receive and/or to mate with a first filter and/or a first filter-containing consumable of a first length, and the second connector socket is configured to receive and/or to mate with a second filter and/or a second filter-containing consumable of a second length.

7. The device of claim 1, comprising a controller configured to control at least one of the flow of oxygen into the chamber, a volume of ozone-enriched air ejected through the outlet, and the flow pressure of the ozone-enriched air based on a type of the filter and/or the filter-containing consumable connected to the at least one connector socket, a number of filters and/or filter containing consumables connected to the device, or a both.

8. A system for reconstituting a filter for use in breath monitoring, the system comprising:
   the filter and/or a filter-containing consumable comprising a connector; and
   a device comprising:
      at least one connector socket configured to receive and/or mate with the connector;

a pump configured to pump ambient air into a chamber of the device;

an inlet configured to allow a flow of oxygen into the chamber, an ultraviolet (UV) source configured to catalyze formation of ozone from the oxygen, thereby generating ozone-enriched air in the chamber; and an outlet configured to eject the ozone-enriched air from the chamber into the filter and/or the filter-containing consumable, thereby reconstituting the filter and/or the filter-containing consumable.

9. The system of claim 8, comprising an ozone filter configured to block ozone from being released into the surroundings.

10. The system of claim 8, comprising a mechanism configured to mark the filter and/or the filter-containing consumable after the filter and/or the filter-containing consumable has been reconstituted.

11. The system of claim 10, wherein the mark comprises a radio-frequency identification (RFID) tag.

12. The system of claim 10, wherein the mark comprises a text label or a colored tag.

13. A method for reconstituting a filter for use in breath monitoring, the method comprising:

connecting a filter and/or a filter-containing consumable to a connector socket of a filter reconstituting device;

injecting ambient air into a chamber of the filter reconstituting device using a pump;

generating a flow of oxygen into the chamber of the device, catalyzing formation of ozone from the oxygen in the chamber using an ultraviolet (UV) lamp, such that the ambient air is enriched with ozone to form ozone-enriched air; and ejecting the ozone-enriched air into the filter, thereby at least partially reconstituting the filter.

14. The method of claim 13, comprising marking the filter and/or the filter-containing consumable after the filter and/or the filter-containing consumable has been reconstituted.

15. The method of claim 14, wherein marking the filter and/or the filter-containing consumable comprising attaching a radio-frequency identification (RFID) tag to the filter and/or the filter-containing consumable.

16. The method of claim 13, comprising blocking the ozone-enriched air from being released into the surroundings utilizing an ozone filter.

17. The method of claim 13, wherein the UV source comprises a low-pressure UV lamp.

18. The method of claim 13, wherein the ozone-enriched air is ejected at high pressure.

19. The method of claim 13, comprising controlling at least one of the flow of oxygen into the chamber, a volume of ozone-enriched air ejected through the outlet, and a flow pressure of the ozone-enriched air ejected based on a type of filter and/or a type of filter-containing consumable connected to the at least one connector socket, a number of filters and/or filter containing consumables connected to the device, or both.

20. The method of claim 13, wherein the UV source is configured to decompose organic compounds present in the chamber, the ambient air, or both.

* * * * *